United States Patent
Zhang et al.

(10) Patent No.: US 11,510,874 B2
(45) Date of Patent: Nov. 29, 2022

(54) METHOD FOR MAKING REDUCTION SENSITIVE NANO MICELLES

(71) Applicant: JIANGNAN UNIVERSITY, Jiangsu (CN)

(72) Inventors: Liping Zhang, Jiangsu (CN); Caihua Ni, Jiangsu (CN); Xinxin Sang, Jiangsu (CN); Gang Shi, Jiangsu (CN)

(73) Assignee: JIANGNAN UNIVERSITY, Wuxi (CN)

( * ) Notice: Subject to any disclaimer, the term of this patent is extended or adjusted under 35 U.S.C. 154(b) by 177 days.

(21) Appl. No.: 17/139,566

(22) Filed: Dec. 31, 2020

(65) Prior Publication Data

US 2022/0054415 A1    Feb. 24, 2022

(30) Foreign Application Priority Data

Aug. 19, 2020   (CN) .......................... 202010835611.3

(51) Int. Cl.
| | |
|---|---|
| *A61K 9/107* | (2006.01) |
| *C08F 220/38* | (2006.01) |
| *C08F 220/58* | (2006.01) |
| *A61K 9/19* | (2006.01) |
| *A61K 31/704* | (2006.01) |
| *A61K 47/32* | (2006.01) |

(52) U.S. Cl.
CPC .............. *A61K 9/1075* (2013.01); *A61K 9/19* (2013.01); *A61K 31/704* (2013.01); *A61K 47/32* (2013.01); *C08F 220/382* (2020.02); *C08F 220/585* (2020.02)

(58) Field of Classification Search
None
See application file for complete search history.

(56) References Cited

U.S. PATENT DOCUMENTS

| 10,632,071 B2 * | 4/2020 | Zhang .................. C08G 73/028 |
| 2011/0150978 A1 * | 6/2011 | Lee ...................... C08F 299/024 |
| | | 514/1.9 |
| 2015/0065442 A1 * | 3/2015 | Xing ....................... A61K 47/34 |
| | | 514/772.3 |

FOREIGN PATENT DOCUMENTS

| CN | 104788689 B | 9/2017 |
| CN | 105524272 B | 8/2018 |

* cited by examiner

*Primary Examiner* — Dale R Miller
(74) *Attorney, Agent, or Firm* — MagStone Law, LLP; Enshan Hong

(57) ABSTRACT

A method for making reduction sensitive nano micelles comprising: 1) dissolving taurine in distilled water, and adding sodium hydroxide solution; 2) dissolving acryloyl chloride in dichloromethane, reacting at 25° C.; dissolving lipoic acid in toluene and adding hydroxyethyl methacrylate, reacting at 85° C.; 3) dissolving N-acryloyltaurine and lipoic acid methacryloyloxyethyl ester and reacting at 60~65° C., dropping the polymer solution into deionized water, adding dithiothreitol and reacting at 25~30° C. to obtain reduction sensitive nano micelles after freeze-drying. The nano micelles have regular morphology and uniform distribution, and can be used as drug carriers for controlled release.

9 Claims, 3 Drawing Sheets

METHOD FOR MAKING REDUCTION SENSITIVE NANO MICELLES

RELATED APPLICATIONS

This application claims the priority from China Patent Application Serial Number CN 202010835611.3, filed on Aug. 19, 2020, the entire content of which is incorporated here by reference.

BACKGROUND OF THE INVENTION

1. Technical Field

The invention relates to the technical field of biomedical materials, particularly, to preparation of reduction sensitive nano micelles and their anticancer drug carriers.

2. Background Art

Cancer is a main cause of death worldwide. At present, the treatment of cancers mainly includes surgical resection, chemical drug therapy and radiation therapy. However, there are many defects in these treatments, such as toxicity and side effects of drugs, damage to normal tissues and organs, which results in great pain for patients.

Drug carriers of nano materials have particular advantages in the delivery of chemotherapy drugs. Encapsulation of anticancer drugs into the carriers with physical/chemical methods can reduce the side effects and improve the bioavailability of drugs.

Taurine is an essential nutrient for human health, and there are amino and sulfonic groups in the molecule of taurine. The sulfonic acid group is a strong ionizable group with a negative charge, which is highly hydrophilic. It can be located in the outer layer of nano micelles to maintain the stability of micelles. Meanwhile, the negatively charged group can adsorb positively charged drug molecules. If sulfonic groups are introduced into drug carriers, the loading rate for an anti-cancer drug doxorubicin hydrochloride can be improved.

Lipoic acid is an important endogenous substance in human body, which can remove free radicals that cause disease in vivo. It is called "universal antioxidant". Lipoic acid has a five-membered ring structure containing sulfur atoms. Under the action of dithiothreitol (DTT), disulfide bonds are formed, which makes the drug carrier cross-linked. However, the disulfide bonds can be broken under the reduction condition in tumor cells, leading to destruction of the cross-linking structure.

Glutathione is a reducing substance, and the concentration of glutathione in tumor cells is 100-1000 times higher than that in body fluid. When drug loaded nano micells enter tumor cells, the cross-linking structure in the nano micells will be destroyed under the action of glutathione of the tumor cells, leading to drug release. Therefore, the drug release can be controlled under the reduction condition.

Although there are many reports on nano micelles already, most of the nano micelles carry drugs by physical adsorption, resulting in low drug loading rates, drug leakage, and less bioavailability of drugs.

SUMMARY OF THE INVENTION

To overcome the problems existing in the prior art, the invention provides a method for making reduction sensitive nano micelles, so as to obtain reduction sensitive nano micelles, consequently, to prepare drug-loaded carriers with stable high drug loading rates.

Firstly, a monomer compound containing sulfonic acid group and C=C double bond is prepared; secondly, lipoic acid is functionalized through an introduction of C=C double bond into the lipoic acid molecule; finally, reduction sensitive nano micelles are prepared through a copolymerization and core cross-linking reaction.

In the specific steps,

1) In a 250 mL single port flask, taurine is dissolved in distilled water, sodium hydroxide solution is added, the flask is placed in an ice water bath at 0° C. and stirred for 30 minutes; the pre refined acryloyl chloride and dichloromethane are mixed to form a solution which is dropped into a single port flask through a constant pressure dropping funnel, and the dropping is completed within 40 minutes, and the reaction is carried out at 25° C. for 5 h. The product is filtered, washed with deionized water for 3 times, then recrystallized with ethyl acetate, and dried in vacuum for 24 h to obtain N-acryloyltaurine;

2) In a three-necked flask equipped with reflux and water separation device, lipoic acid is dissolved in toluene, then hydroxyethyl methacrylate and a catalyst are added under stirring for 30 minutes protected by nitrogen. The mixture is heated to 85° C. for reaction 6 hours. After cooling, the product is washed with 1.0 M sodium hydroxide solution. The water layer is discarded by separation from the mixture, and toluene is removed by vacuum distillation to obtain lipoic acid methacryloyloxyethyl ester;

3) N-acryloyltaurine and lipoic acid methacryloyloxyethyl ester are dissolved in dimethyl sulfoxide in a three-necked flask, stirred evenly at room temperature. An initiator is added under stirring to make it completely dissolved. The mixed solution is filled with nitrogen for 20 minutes, heated to 60~65° C., reacted for 5 hours, and then cooled to obtain copolymer solution; the above copolymer solution is slowly dropped into deionized water, and dithiothreitol is added for reacting 24 h at 25~30° C. to obtain a nano micelle solution, the nano micelle solution is transferred to dialysis bags for dialyzing 72 hours. Finally, reduction sensitive nano micelles can be obtained after freeze-drying.

In the step 1) of the making method, the molar ratio of taurine to sodium hydroxide is 1:1.

In the step 1) of the making method, the molar ratio of taurine to acryloyl chloride is 1:1.1~1.2.

In the step 2) of the making method, the molar ratio of lipoic acid to hydroxyethyl methacrylate is 1.2~1.4:1.

In the step 2) of the making method, the catalyst is one or more of p-toluenesulfonic acid, concentrated sulfuric acid, perchloric acid and trichloroacetic acid, the consumption of the catalyst is 1~3 wt % of the weight of lipoic acid.

In the step 3) of the making method, the weight ratio of N-acryloyltaurine to lipoic acid methacryloyloxyethyl ester is 1:1~2.

In the step 3) of the making method, the initiator is one or more of azodiisobutylimidazoline hydrochloride, azodiisobutyronitrile and azodiisoheptanitrile, the consumption of initiator is 0.5~1 wt % of the sum weight of N-acryloyltaurine and lipoic acid methacryloyloxyethyl ester.

In the step 1) of the making method, the weight ratio of lipoic acid methacryloxyethyl ester to dithiothreitol is 17:1~6:1.

As a second aspect of the invention, the reduction sensitive nano micelles prepared by the above making method is provided.

As a third aspect of the invention, a method of making anti-cancer drug-loaded nano micelles is provided, comprising:

Dissolving 10 mg of anti-cancer drug doxorubicin hydrochloride in 10 mL of dimethyl sulfoxide, adding 0.1 mL triethylamine under stirring, and reacting for one hours; adding reduction sensitive nano micelles to the anti-cancer drug solution, then adding 80 mL of ultrapure water and stirring for 2 hours; transferring the solution into a dialysis bag with a cutoff molecular weight of 3500 and dialyzing for 8 hours; freeze-drying the solution to obtain anti-cancer drug-loaded nano micelles.

With the above scheme, the invention has at least the following advantages:

The out shell of the reduction sensitive nano micelles of this invention contains hydrophilic taurine as structural units which carry negatively charged sulfonic acid groups. On the one hand, the sulfonic acid groups can stabilize the micelles, on the other hand, they can adsorb positively charged doxorubicin, and improve the drug loading rate.

The core of the reduction sensitive nano micelles of the invention is hydrophobic lipoic acid. After the reaction with dithiothreitol, the core of the nano micelle is crosslinked, which ensures the stability of the nano micelles under non reducing conditions; however, by the action of glutathione in tumor cells, the crosslinking structure is destroyed and the drug is released, therefore, the drug release can be controlled by reduction conditions.

The reduction sensitive nano micelles of the invention have regular morphology and uniform distribution, and are used as drug carriers with excellent performance.

DESCRIPTION OF PREFERRED EMBODIMENTS

Figure 1:
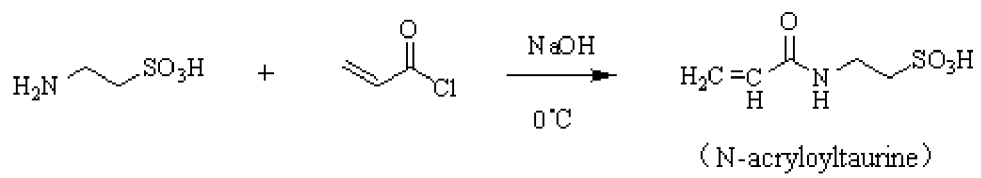
FIG. 1 Schematic diagram for the preparation of N-acryloyltaurine.
Figure 2:
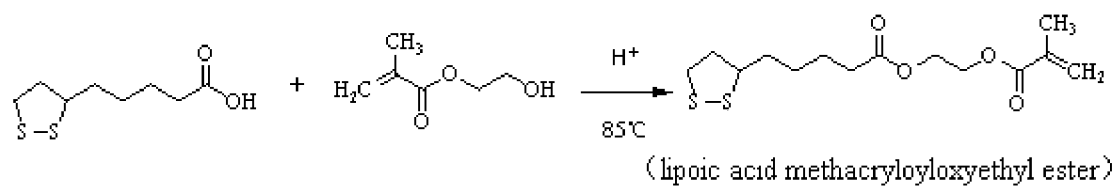
FIG. 2 Schematic diagram for the preparation of lipoic acid methacryloyloxyethyl ester.
Figure 3:
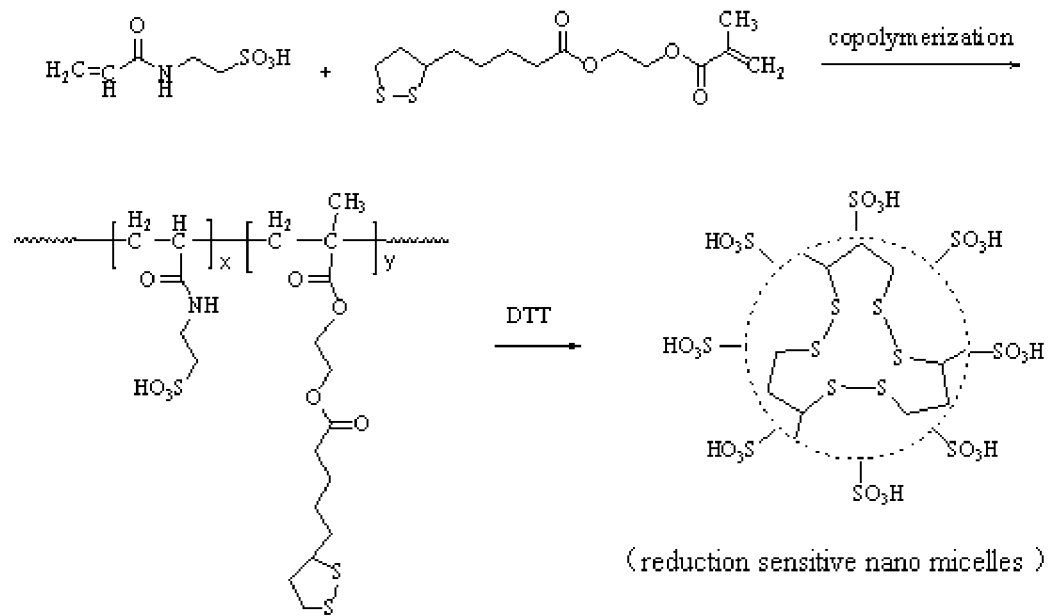
FIG. 3 Synthetic route of the reduction sensitive nano micelles.

The detailed preferred embodiments of the invention are described as follows. The following embodiments are used to illustrate the invention, but not to limit the scope of the invention.

Embodiment 1

Step 1) Preparation of N-acryloyltaurine: in a 250 mL single port flask, 6.25 g of taurine is dissolved in 50 mL distilled water, 25 mL of sodium hydroxide solution with concentration of 2.0 mol/L is added, the flask is placed in an ice water bath at 0° C. and stirred for 30 minutes; 5.0 g of pre refined acryloyl chloride and 20 mL of dichloromethane are mixed to form a solution, the solution is dropped into a single port flask through a constant pressure dropping funnel. The dropping is completed within 40 min, and the reaction is carried out at 25° C. for 5 hours. The product is filtered, washed with deionized water for 3 times, then recrystallized with ethyl acetate, and dried in a vacuum oven for 24 h to obtain N-acryloyltaurine;

Step 2) Preparation of lipoic acid methacryloyloxyethyl ester: In a three-necked flask equipped with reflux and water separation device, 12.4 g of lipoic acid is dissolved in 100 mL of toluene, then 6.5 g of hydroxyethyl methacrylate and a 0.25 g of p-toluenesulfonic acid are added under stirring for 30 minutes in nitrogen atmosphere. The mixture is heated to 85° C. for reaction 6 hours. After cooling, the product is washed with 1.0 M sodium hydroxide solution. The water layer is discarded by separation from the mixture, and toluene is removed by vacuum distillation to obtain lipoic acid methacryloyloxyethyl ester;

Step 3) Preparation of reduction sensitive nano micelles: 2.5 g of N-acryloyltaurine and 2.5 g of lipoic acid methacryloyloxyethyl ester are dissolved in 20 mL of dimethyl sulfoxide in a 150 mL three-necked flask, stirred evenly at room temperature. The initiator azodiisobutylimidazoline hydrochloride 0.05 g is added under stirring to make it completely dissolved. The mixed solution is filled with nitrogen for 20 minutes, heated to 60~65° C., reacted for 5 hours, and then cooled to obtain copolymer solution; the above copolymer solution is slowly dropped into 250 mL of deionized water, and 0.15 g of dithiothreitol (DTT) is added for reacting 24 hours at 25~30° C. to obtain a nano micelle solution, the nano micelle solution is transferred to a dialysis bag with cutoff molecular weight 3500 for dialyzing 72 hours. Finally, reduction sensitive nano micelles can be obtained after freeze-drying, the sample is labeled as NLD-1.

Embodiment 2

The steps 1) and 2) are the same as those in embodiment 1, but in step 3), the weight of lipoic acid methacryloyloxyethyl ester is changed to 3.0 g, the weight of azodiisobutylimidazoline hydrochloride is changed 0.055 g, and the weight of dithiothreitol is changed to 0.3 g. The reduction sensitive nano micelles labeled as NLD-2 is obtained.

Embodiment 3

The steps 1) and 2) are the same as those in embodiment 1, but in step 3), the weight of lipoic acid methacryloyloxyethyl ester is changed to 3.5 g, the weight of azodiisobutylimidazoline hydrochloride is changed 0.06 g, and the weight of dithiothreitol is changed to 0.45 g. The reduction sensitive nano micelles labeled as NLD-3 is obtained.

Embodiment 4

The steps 1) and 2) are the same as those in embodiment 1, but in step 3), the weight of lipoic acid methacryloyloxyethyl ester is changed to 4.0 g, the weight of azodiisobutylimidazoline hydrochloride is changed 0.065 g, and the weight of dithiothreitol is changed to 0.6 g. The reduction sensitive nano micelles labeled as NLD-4 is obtained.

Embodiment 5

The steps 1) and 2) are the same as those in embodiment 1, but in step 3), the weight of lipoic acid methacryloyloxyethyl ester is changed to 5.0 g, the weight of azodiisobutylimidazoline hydrochloride is changed 0.075 g, and the weight of dithiothreitol is changed to 0.8 g. The reduction sensitive nano micelles labeled as NLD-5 is obtained.

TABLE 1

List of making embodiments of reduction sensitive nano micelles

| Sample ID | NAT (g) | LAMHE (g) | initiator (g) | DTT (g) |
|---|---|---|---|---|
| NLD-1 | 2.5 | 2.5 | 0.050 | 0.15 |
| NLD-2 | 2.5 | 3.0 | 0.055 | 0.30 |
| NLD-3 | 2.5 | 3.5 | 0.060 | 0.45 |
| NLD-4 | 2.5 | 4.0 | 0.065 | 0.60 |
| NLD-5 | 2.5 | 5.0 | 0.075 | 0.80 |

Notes:
NAT is N-acryloyltaurine;
LAMHE is lipoic acid methacryloyloxyethyl ester;
initiator is azodiisobutylimidazoline hydrochloride;
DTT is dithiothreitol.

Embodiment 6

Figure 4:
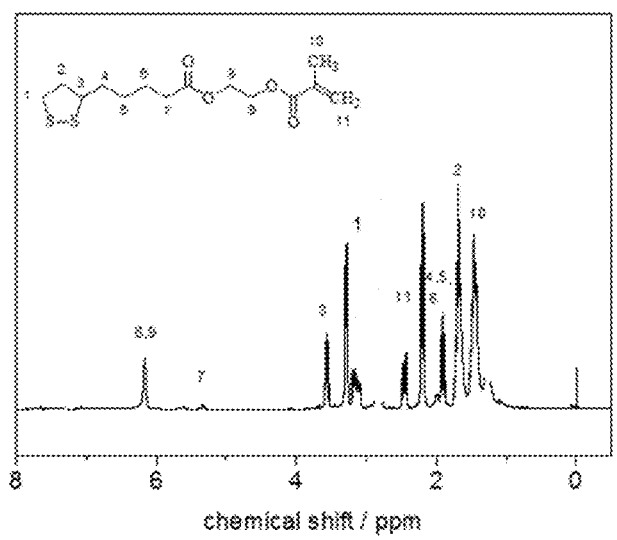
FIG. 4 The $^1$H NMR spectra of lipoic acid methacryloyloxyethyl ester.

$^1$H NMR characterization of lipoic acid methacryloyloxyethyl ester: the lipoic acid methacryloyloxyethyl ester is dissolved in deuterated chloroform with a concentration of 2020 mg/mL, and the internal standard is tetramethylsilane. The $^1$H NMR spectrum of lipoic acid methacryloyloxyethyl ester is determined by AVANCE III HD 400 MHz nuclear magnetic resonance spectrometer. The results are shown in FIG. 4. The analysis is as follows: chemical shift δ:3.5~3.7 (2H, —SS—$CH_2$—), δ:1.56~1.75 (2H, —$CH_2$—), δ:3.6~3.7 (1H, —SS—CH—), δ:1.7~1.9 (6H, —$CH_2$—$CH_2$—$CH_2$—), δ:1.5~1.6 (3H, $CH_3$), δ:2.4~2.5 (2H, $CH_2$=); δ:6.1~6.3 (4H, —$CH_2$—$CH_2$—), δ:5.2~5.3 (—$CH_2$—C=O); the chemical shifts and integral area of hydrogen are the same as the theoretical value, which proves the formation of lipoic acid methacryloyloxyethyl ester.

Embodiment 7

Zeta potential analysis of the nano micelles: zeta potentials of the nano particles are analyzed by ZetaPALS type of zeta potential analyzer and nano particle size analyzer. The test temperature is 25° C. and pH is 7.4. It can be seen from Table 2 that the nano micelles have a high negative zeta potentials, indicating that the outer layer of the nano micelles is negatively charged, showing existance of $SO_3^-$ which is derived from taurine. It can also be observed that from NLD-1 to NLD-5, the absolute value of zeta potential decreases. This is because from NLD-1 to NLD-5, the content of LAMHE increases, the relative content of NAT decreases, and the concentration of $SO_3^-$ decreases in turn, so the absolute value of zeta potential decreases.

TABLE 2

Properties of the reduction sensitive nano micelles

| Sample ID | NAT:LAMHE (weight ratio) | Zeta potential | $R_h^{a)}$ (nm) | $DLR^{b)}$ (%) |
|---|---|---|---|---|
| NLD-1 | 1:1.0 | −24.8 | 92 | 21.5 |
| NLD-2 | 1:1.2 | −23.1 | 130 | 20.4 |
| NLD-3 | 1:1.4 | −18.5 | 171 | 19.3 |
| NLD-4 | 1:1.6 | −17.2 | 183 | 18.2 |
| NLD-5 | 1:2.0 | −16.4 | 197 | 16.8 |

Notes:
$^{a)}$Measured by Dynamic laser light scattering method (pH = 7.2, 25° C.);
$^{b)}$DLR: Drug loading rate Embodiment 8

Particle size analysis of the nano micelles: the nano micelle solution with concentration of 1.0 mg/mL is prepared, and is filtrated by 0.45 μm filter for removing dust. The particle size and distribution of the nano micelles are measured at 25° C. by ALV/DLS/sls-5022f dynamic laser light scattering instrument, and the results are shown in Table 2. The particle sizes of the micelles are ranged from 92 nm to 197 nm. The particle size increases with the increase of the content of lipoic acid methacryloyloxyethyl ester. This is because the lipoic acid methacryloyloxyethyl ester is hydrophobic. When the content of lipoic acid methacryloyloxyethyl ester increases, the hydrophobic interaction among the chain segments is enhanced, resulting in increase of the particle size.

Embodiment 9

Figure 5:
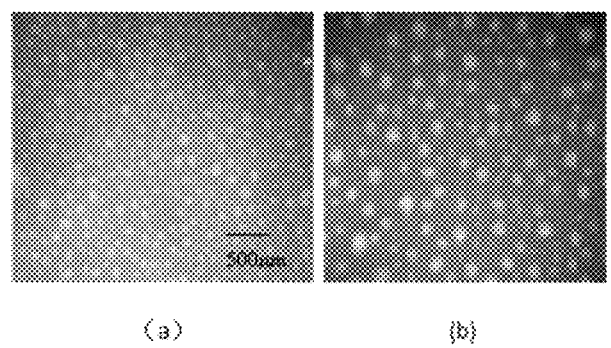
FIG. 5 Transmission electron microscopy of the reduction sensitive nano micelles.

Morphology observation of the nano micelles: 30 μL of the nano micelle solution with concentration of 1.5 mg/mL is dropped onto the copper mesh, and a drop of 1.0 wt % phosphotungstic acid solution is added to the copper mesh for dyeing. The copper mesh is naturally dried at room temperature. The morphologies of NLD-1 and NLD-5 nanoparticles are observed by transmission electron microscope (TEM) under high a vacuum condition. The accelerating voltage of transmission electron microscope is 120 kV. FIGS. 5(*a*) and (*b*) show TEM images of NLD-1 and NLD-5, respectively. It can be observed that the nano micelles are spherical with regular morphology, and the particle size change is consistent with the results measured by dynamic laser light scattering method, that is, with the increase of the content of lipoic acid methacryloyloxyethyl ester, the particle size increased.

Embodiment 10

Figure 6:
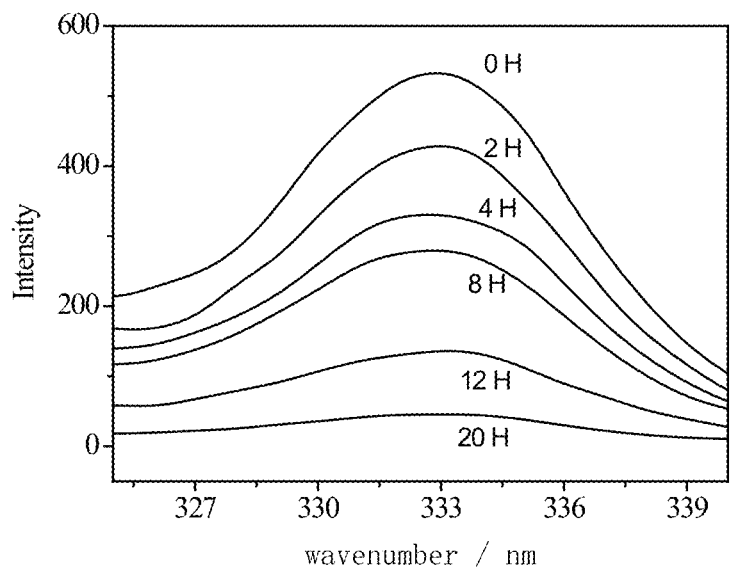
FIG. 6 The change of fluorescence intensity of the reduction sensitive nano micelles under the action of 10 mmol/L glutathione.

Reductive sensitivity test of the nano micelles: 8 mL of the nano micelle solution (1 mg/mL) containing 4.0×10$^{-6}$ mmol/L pyrene are incubated in a oscillation chamber at 37° C. for a period of time, glutathione (GSH) is added to the solution with GSH concentration of 10 mmol/L. The excitation spectra of the solution at different incubation time are determined by fluorescence spectrophotometer. The emission wavelength is 395 nm, and the excitation and emission slit widths are 5 nm. The fluorescence intensity change is observed. Pyrene is a hydrophobic substance which will enter into the inner cavity of micelles and display the excitation spectrum. When the micelles are destroyed, pyrene molecules enter into the polar medium and the fluorescence intensity decreases. It can be seen from FIG. 6 that the fluorescence intensity of the micelles in 10 mmol/L of GSH solution decreases with increase of incubation time.

This is because the disulfide bond in the micelles breaks under the action of GSH, the crosslinking structure is destroyed, and pyrene is released into polar water medium, resulting in the decrease of fluorescence intensity.

Embodiment 11

Drug loading of the nano micelles: 10 mg doxorubicin hydrochloride is dissolved in 10 mL dimethyl sulfoxide, 0.1 mL triethylamine is added and reacted for 1 h under stirring; 10 mg of the nano micelle and 80 mL ultra-pure water are added, stirring for 2 h, the solution is transferred into a dialysis bag with cutoff molecular weight of 3500, dialyzing for 8 h, and drug loaded micelle solution is obtained. Then, 2.0 mL of the drug loaded micelle solution is lyophilized and weighed, and redissolved in certain volume of dimethyl sulfoxide. The absorbance at 483 nm is measured with UV spectrophotometer. Based on a standard curve, the drug loading rate (DLR) of doxorubicin is calculated:

$$DLR(\%) = (W_L/W_N) \times 100$$

$W_L$—weight of drug loaded in carrier, mg;
$W_N$—weight of drug loaded micelles after lyophilization, mg;

The anticancer drug doxorubicin is loaded in the nano micelles with high drug loading rates which are in the range of 16.8%~21.5% in the 5 samples, as shown in Table 2. This is because the nano micelles carry a large number of $SO_3^-$ groups that can react with the positively charged amino groups in doxorubicin molecules, leading to obtain high drug loading rates.

Embodiment 12

Figure 7:
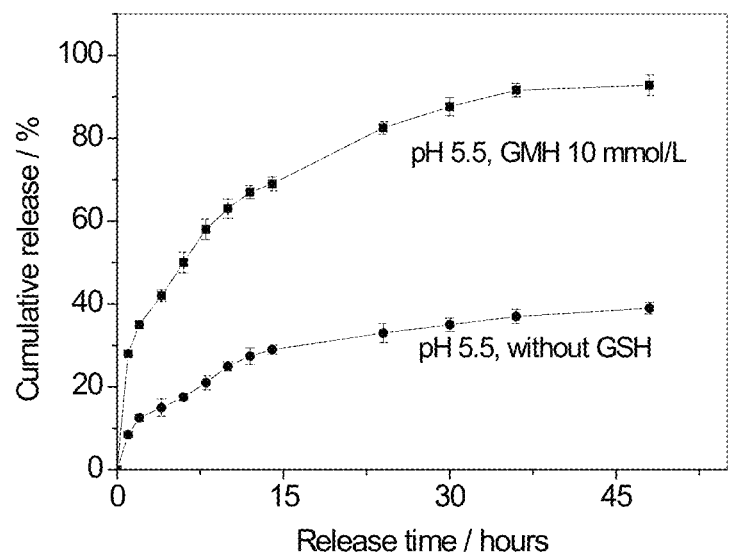
FIG. 7 The drug release curve of doxorubicin loaded nano micelles.

Drug controlled release: 5 ml of drug loaded micelle solution (1 mg/mL) is put in a dialysis bag, the bag is placed in an ABS buffer solution containing 10 mmol/L GSH (pH 5.5) as drug release medium, oscillating at 37° C.; 4 ml of the release medium is taken out at different time intervals for measuring concentration of doxorubicin in the medium with ultraviolet spectrophotometer, and the cumulative release is calculated and showed in FIG. 7. The results indicate that the cumulative release is 71% in 15 hours and 92.8% in 48 hours, respectively. As a contrast, if the release is carried out under the same conditions but without GSH, the cumulative release is 30% in 15 hours and 36.9% in 48 hours, respectively, indicating that the cumulative release can be controlled by reductive conditions.

Obviously, the described embodiments are only parts of the embodiments in the invention. Any other modifications, equivalent replacements and improvements made within the spirit and principle of the invention shall be included in the scope of the invention.

What is claimed is:

1. A method for making reduction sensitive nano micelles comprising steps of:
   1) dissolving taurine in distilled water in a 250 mL single port flask, adding sodium hydroxide solution and stirring in an ice water bath for 30 minutes; dissolving acryloyl chloride in dichloromethane to form a solution, adding the solution to the single port flask through a constant pressure funnel within 40 minutes, reacting at 25° C. for 5 hours, filtrating and washing the product with deionized water for 3 times, recrystallizing with ethyl acetate, drying in vacuum for 24 hours to obtain N-acryloyltaurine;
   2) dissolving lipoic acid in toluene in a three-necked flask equipped with a reflux and water separation device, adding hydroxyethyl methacrylate and a catalyst, stirring for 30 minutes, reacting at 85° C. for 6 hours under protection of nitrogen, cooling and washing the product with 1.0 M sodium hydroxide solution, discarding water layer through separation, removing the toluene by vacuum distillating to obtain lipoic acid methacryloyloxyethyl ester; and
   3) dissolving N-acryloyltaurine of step 1) and lipoic acid methacryloyloxyethyl ester of step 2) in dimethyl sulfoxide in a three-necked flask, stirring evenly at room temperature, adding an initiator and stirring until completely dissolved; ventilating nitrogen for 20 minutes, raising temperature to 60~65° C. and reacting for 5 hours to obtain a copolymer solution, after cooling, dropping the copolymer solution slowly into deionized water, adding dithiothreitol and reacting at 25~30° C. for 24 hours, transferring the product solution into a dialysis bag for dialyzing 72 hours, to obtain reduction sensitive nano micelles after freeze-drying.

2. The method of claim 1, wherein in step 1), the molar ratio of taurine to sodium hydroxide is 1:1.

3. The method of claim 1, wherein in step 1), the molar ratio of taurine to acryloyl chloride is 1:1.1~1.2.

4. The method of claim 1, wherein in step 2), the molar ratio of lipoic acid to hydroxyethyl methacrylate is 1.2~1.4:1.

5. The method of claim 1, wherein in step 2), the catalyst is one or more of p-toluenesulfonic acid, concentrated sulfuric acid, perchloric acid and trichloroacetic acid, the consumption of the catalyst is 1~3 wt % of the weight of lipoic acid.

6. The method of claim 1, wherein in step 3), the weight ratio of N-acryloyltaurine to lipoic acid methacryloyloxyethyl ester is 1:1~2.

7. The method of claim 1, wherein in step 3), the initiator is one or more of azodiisobutylimidazoline hydrochloride, azodiisobutyronitrile and azodiisoheptanitrile, the consumption of initiator is 0.5~1 wt % of the sum weight of N-acryloyltaurine and lipoic acid methacryloyloxyethyl ester.

8. The method of claim 1, wherein in step 3), the weight ratio of lipoic acid methacryloxyethyl ester to dithiothreitol is 17:1~6:1.

9. A method of making anti-cancer drug-loaded nano micelles comprising:
   a) obtaining reduction sensitive nano micelles based on the method of claim 1,
   b) dissolving 10 mg of anti-cancer drug doxorubicin hydrochloride in 10 mL dimethyl sulfoxide, adding 0.1 mL triethylamine under stirring, and reacting for one hours,
   c) adding reduction sensitive nano micelles of step a) to the anti-cancer drug solution of step b), then adding 80 mL of ultrapure water and stirring for 2 hours,
   d) transferring the solution of step c) into a dialysis bag with a cutoff molecular weight of 3500 and dialyzing for 8 hours,
   e) freeze-drying the solution of step d) to obtain anti-cancer drug-loaded nano micelles.

* * * * *